(12) United States Patent
Chang

(10) Patent No.: US 9,222,072 B2
(45) Date of Patent: Dec. 29, 2015

(54) MANUFACTURING METHOD OF IMMUNE KILLER CELLS

(75) Inventor: Hsun-Lang Chang, New Taipei (TW)

(73) Assignee: IVY LIFE SCIENCES CO., LTD., New Taipei (TW)

( * ) Notice: Subject to any disclaimer, the term of this patent is extended or adjusted under 35 U.S.C. 154(b) by 259 days.

(21) Appl. No.: 13/024,087

(22) Filed: Feb. 9, 2011

(65) Prior Publication Data

US 2011/0201114 A1 Aug. 18, 2011

(30) Foreign Application Priority Data

Feb. 12, 2010 (TW) .............................. 99104629 A

(51) Int. Cl.
*C12N 5/0783* (2010.01)
*C12N 5/078* (2010.01)

(52) U.S. Cl.
CPC .......... *C12N 5/0636* (2013.01); *C12N 2501/23* (2013.01); *C12N 2501/24* (2013.01)

(58) Field of Classification Search
USPC ................................................ 435/372, 377
See application file for complete search history.

(56) References Cited

U.S. PATENT DOCUMENTS

2003/0068306 A1* 4/2003 Dilber ........................ 424/93.7

FOREIGN PATENT DOCUMENTS

| CN | 1552848 A | 12/2004 |
| CN | 101314764 A * | 12/2008 |

OTHER PUBLICATIONS

Nair et al.; Immunoregulation of natural and lymphokine-activated killer cells by selenium; Immunopharmacology; vol. 19, (1990); pp. 177-183.*
CN101314764A translation (translated Nov. 14, 2012).*

* cited by examiner

*Primary Examiner* — Antonio Galisteo Gonzalez
(74) *Attorney, Agent, or Firm* — Muncy, Geissler, Olds & Lowe, P.C.

(57) ABSTRACT

The present invention relates to a manufacturing method of immune killer cells characterized in that an immune killer cell is induced in a culture medium containing concanavalin A (ConA), and the immune killer cell is maintained or expanded in a culture procedure. Antibody proteins are not used as a stimulant in the culture process to avoid the risk of being infected by zoonotic diseases and effectively increase the number and specific release of the immune killer cells.

11 Claims, 1 Drawing Sheet

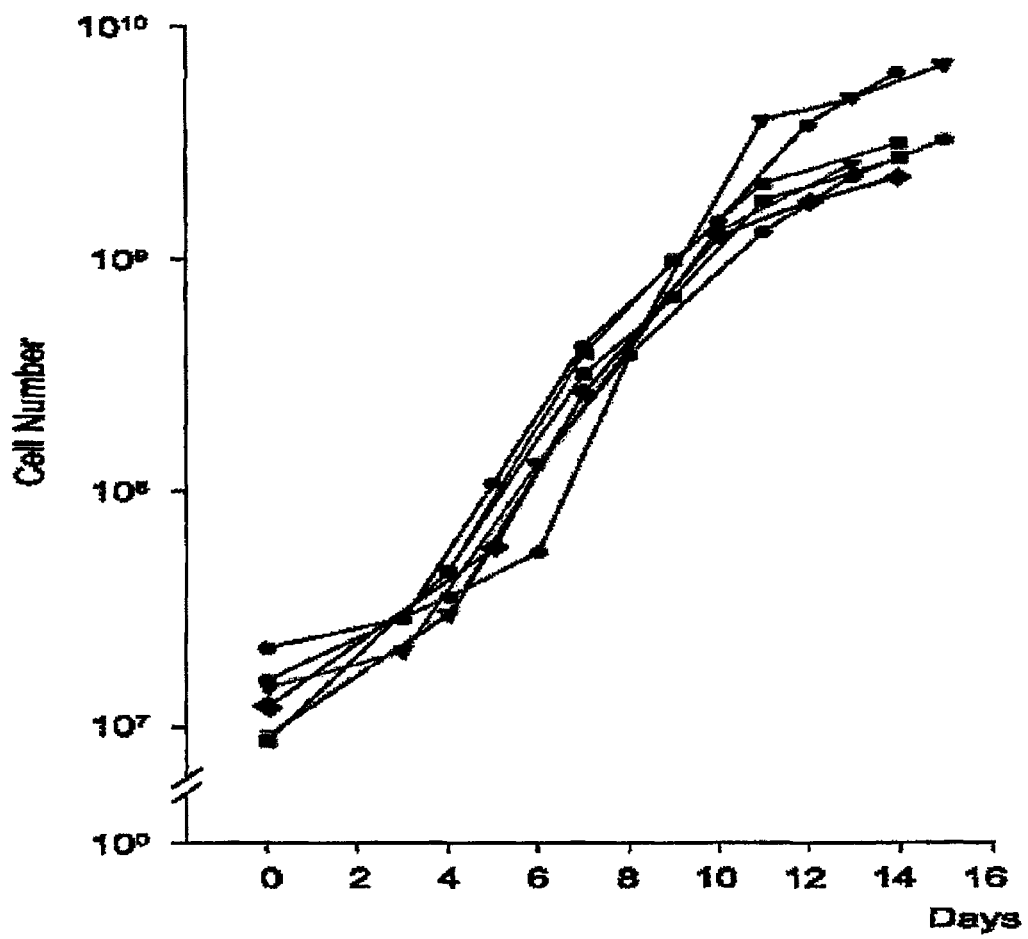

MANUFACTURING METHOD OF IMMUNE KILLER CELLS

BACKGROUND OF THE INVENTION (a) Field of the Invention

The present invention relates to a manufacturing method of immune killer cells, and particularly to a medical composite that applies immune killer cells to suppress tumors.

(b) Description of the Prior Art

Present researches on the subject of immune therapies for cancer treatment include injections of cytokines such as interferon or interleukin to enhance the anti-cancer effect by stimulating immunity directly. However, cytokines generally have significant side effects. For example, a cytokine including interferon and interleukin will usually induce symptoms similar to a flu and cause fever, chill, tiredness and digestive tract problems, and a patient's blood pressure may also be affected. In general, the side effect caused by interleukin-2 (IL-2) is more seriously, and doctors have to observe their patients carefully during treatment process. Although the injection of cytokines has brought cancer treatment a ray of hope, yet it is usually not recognized as a totally feasible solution.

In addition to the injection of cytokines, the present immune therapies also include cancer vaccine therapy which may be able to improve immunity, but a cancer patient's immune system is suppressed, and the effect of the treatment remains to be seen. Among the present immune therapies, the immune cell therapy technique should be a quicker and more effective one. The so-called immune cell therapy technique refers to the therapy that extracts white blood cells from a patient for culturing and proliferating a large quantity of lymphokine activate killer (LAK) cells, cytotoxic T lymphocyte (CTL) cells or natural killer (NK) cells, and then infuses these cells back into the patient's body to provide an anti-cancer effect.

Since cells such as NK cells and CTL cells (and LAK cells are not a normal group which exists in the human body, but they are cells reproduced in a large quantity after the culture of CTL cells in a high concentration of CTL) with the capability of killing cancer cells which exist in the human body, therefore the CTL cells and NK cells in human body come with a limited quantity and a suppressed specific release, and immunologists have been trying for a long time to culture a large quantity of these cells by cytokine outside human bodies, and then injecting the cells back into human bodies to improve the patients' anticancer specific release. This method has the advantage of achieving a quick result without any exclusion (because the cells are obtained from the patients themselves. Since it is necessary to remove the cytokine before the injection of cells takes place, there will be no side effect of the cytokine. The keys of this method include proliferating sufficient cells and providing an appropriate specific release to maximize the anti-cancer effect. However, this method has not been used extensively in clinical applications, mainly due to the bottlenecks on the proliferation of a large quantity of the cells and the improvement of the specific release of the proliferated cells.

In the culture process of in vitro immune cells, antibody proteins of animals are generally used as a stimulant, and such arrangement may cause the infection of zoonotic diseases and jeopardize the health and even the life of the patients. For example, as disclosed in P.R.C. Pat. No. ZL 200310109565.5, two types of mitogen-associated specific release cells including phytohemagglutinin (PHA) and Anti-CD3 monoclonal antibody (anti-CD3 mAb) are used for improving the strength of stimulating the cells to enhance the proliferation capability of the in vitro cells. However, the source of using anti-CD3 mAb generally comes from mouse experiments, and the genes of mice and human beings are very close, so that it is difficult to avoid the infection of zoonotic diseases (or common diseases between mice and men that may jeopardize human health and life).

SUMMARY OF THE INVENTION

Therefore, it is a primary objective of the present invention to provide a manufacturing method of immune killer cells, characterized in that the immune killer cells are induced in a culture medium containing concanavalin A (ConA) and the culture procedure for maintaining or expanding the immune killer cells can be achieved without the need of using any antibody protein.

In the foregoing method, the culture medium further comprises interleukin, interferon or phytohemagglutinin (PHA).

In the foregoing method, the culture medium does not include any antibody protein used as a stimulant.

In the foregoing method, the concanavalin A (ConA) in the culture medium has a concentration of 0.1~100 μg/mL, and preferably equal to 0.1~30 μg/mL.

In the foregoing method, the method further comprises the step of separating peripheral blood mononuclear cells.

In the foregoing method, the peripheral blood mononuclear cells in the culture medium have a concentration of $0.1 \times 10^6 \sim 10 \times 10^6$ cells/mL.

Another objective of the present invention is to provide an immune killer cell manufactured by the aforementioned method.

The immune killer cells include natural killer (NK) cells, natural killer T (NKT) cells, gamma-delta T (γδT) cells and cytotoxic T cells (Tc cells or CTL).

The immune killer cells are composed of 5~20% of NK cells, 15~50% of NKT cells, 10~30% of γδT cells and 40~70% of Tc cells.

Another objective of the present invention is to provide a medical composite for suppressing tumors, and the medical composite contains an effective dose of the aforementioned immune killer cells.

Another objective of the present invention is to provide a kit containing the aforementioned medical composite.

More specifically, the present invention relates to a preparation method of autologous immune killer cells and its applications, wherein peripheral blood mononuclear cells (PBMC) are separated from a patient's blood under sterile conditions, and then cultured by a culture medium, and the culture medium contains concanavalin A (ConA), interleukin-2 (IL-2), interferon-γ or phytohemagglutinin (PHA), without using any antibody protein from mice or other animals as a stimulant, so as to avoid the risk of being infected by zoonotic diseases and effectively increase the number and specific release of the immune killer cells.

An appropriate quantity of cytokines such as ConA and IL-2 added into the culture medium as the stimulant in the present invention can promote the proliferation and specific release of the immune killer cells such as the NK cells, NKT cells, Tc cells and γδT cells, and a good specific release effect can be achieved if the proportion of composition of the cells is equal to a certain specific percentage. If the concentration and proportion of the aforementioned stimulant are changed, the percentage composition and proliferation quantity of the cells can be adjusted to fit different applications.

To enable a further understanding of the said objectives and the technological methods of the invention herein, the brief description of the drawings below is followed by the detailed description of the preferred embodiments.

BRIEF DESCRIPTION OF THE DRAWING

FIG. 1 shows a culture growth curve of immune killer cells of the present invention.

DETAIL DESCRIPTION OF THE PREFERRED EMBODIMENTS

The present invention will become clearer in light of the following detailed description of illustrative embodiments of this invention described in connection with the related drawings. Only some embodiments of the present invention have been illustrated in the drawings, but it should be pointed out that many other modifications are conceivable within the scope of the following claims.

1. Cell Culture Experiment of Immune Killer Cells

The procedure of culturing immune killer cells is described below:

(1) Peripheral blood mononuclear cells (PBMC) in peripheral blood are extracted and put into a cell culture flask, and the concentration of cells is adjusted to $0.5 \times 10^6 \sim 2 \times 10^6$ cells/mL by a culture medium, and carbon dioxide are introduced into an incubator for the cell culture. The culture medium can be RPMI-1640 culture medium, IMDM culture medium, ALYS culture medium or AIM-V culture medium, and the culture medium comprises the following ingredients:

| | |
|---|---|
| Concanavalin A | 0.1~30 µg/mL |
| Proleukin | 200~1000 IU/mL |
| Interferon-γ | 600~1500 units |
| Human Auto Serum | 5~12% |

(2) After the cell culture in the culture medium for two to six days, a culture medium or saline solution is used for rinsing the cells for 1~2 times, and then a fresh culture medium is used for dispersing the cells and adjusting the concentration of the cells to $0.3 \times 10^6 \sim 2 \times 10^6$ cells/mL, and then the cells are put into the carbon dioxide incubator for the cell culture. The culture medium can be RPMI-1640 culture medium, IMDM culture medium, ALYS culture medium or AIM-V culture medium, and the culture medium comprises the following ingredients:

| | |
|---|---|
| Interleukin-2 | 200~600 IU/mL |
| Interferon-γ | 100~300 U/mL |
| Interleukin-15 | 10~50 ng/mL |

(3) And then, a fresh culture medium is added approximately every 2 to 3 days depending on the cell growing density, and the concentration of the cells is adjusted within a range of $0.3 \times 10^6 \sim 2 \times 10^6$ cells/mL, and finally the cells are put into the carbon dioxide incubator for the cell culture. The culture medium can be RPMI-1640 culture medium, IMDM culture medium, ALYS culture medium or AIM-V culture medium, and the culture medium comprises the following ingredients:

| | |
|---|---|
| Interleukin-2 | 100~500 IU/mL |
| Interferon-γ | 80~150 U/mL |
| Interleukin-15 | 10~30 ng/mL |

(4) And then, the aforementioned step (3) is repeated once for every 2 to 3 days until the total number of culturing days is equal to 14.

The immune killer cells manufactured by the aforementioned method are mixed cells including NK cells (having the negative phenotype of CD3 and the positive phenotype of CD56), NKT cells (having the positive phenotype of CD3 and the positive phenotype of CD56), γδT cells (having T cells of a γδT cell receptor) and Tc cells (having Tc cells or CTL cells of an αβT cell receptor, which are killer cells with the most powerful specific release in an immune system.

In the immune killer cells manufactured by the aforementioned culture method, the composition percentage of each cell varies due to the difference of individuals, but overall speaking, the composition percentage of most people is as follows: 5~20% of NK cells, 15~50% of NKT cells, 10~30% of γδT cells, and 40~70% of Tc cells. The procedures for inducing, maintaining or expanding the immune killer cells can be achieved without using any antibody protein. The concanavalin A in the culture medium has a concentration 0.1~100 µg/mL, and the concentration of the concanavalin A is equal to 0.1~30 µg/mL in this preferred embodiment.

With reference to FIG. 1 for a culture growth curve of immune killer cells of the present invention, 30 c.c. of blood is extracted from an arm vein of each of six volunteers and processed and cultured according to the aforementioned method. Samples are taken from the cell culture solution and the total quantity of cells is counted once every 1~3 days after the culture starts, and a graph of the total quantity of cells versus the number of culturing days is plotted. In the graph, the Y-axis represents the quantity of immune killer cells, and the X-axis represents the number of culturing days, and the graph shows that the total number of immune killer cells increases significantly until the total quantity of immune killer cells exceeds 109 cells in the $14^{th}$ day after the culture takes place.

2. Cytotoxic Cell Experiment of Immune Killer Cells

After the culture, the PBMC becomes immune killer cells (IKC), and the specific release for anti lung cancer or liver cancer is increased substantially. In Table 1, the specific release (S) of lung cancer killer cells such as NC1-H23 and Hep3B cells is shown, provided that the immune killer cells and PBMC of the six volunteers are at E/T=50. The result of Table 1 is obtained by using a standard 4h 51 Cr-release assay analysis.

TABLE 1

| | Specific Release | | | |
|---|---|---|---|---|
| Volunteer's No. | E = PBMC T = NCI-H23 | E = IKC T = NCI-H23 | E = PBMC T = Hep3B | E = IKC T = Hep3B |
| 1 | 2% | 18% | 2% | 32% |
| 2 | 0% | 18% | 1% | 24% |
| 3 | 0% | 16% | 3% | 20% |
| 4 | 0% | 8% | 3% | 17% |
| 5 | | | 6% | 15% |
| 6 | | | 8% | 33% |

3. Animal Experiment of Immune Killer Cells (1) Cell Tumorigenicity Experiment (Safety Experiment) of Immune Killer Cells To test whether or not the injection of immune killer cells (IKC) causes tumors, and 20 BALB/c nude mice are divided into two groups, and each group includes ten mice, and the immune killer cells are injected into one of the two groups of the mice by a subcutaneous (s.c.) injection (wherein $2 \times 10^7$ immune killer cells are injected to each mouse), and the immune killer cells are injected into the other group by an intravenous (i.v.) injection (wherein $2 \times 10^7$ immune killer cells are injected to each mouse). The mice are sacrificed in 30 days after the vaccination, and examined whether or not there is any tumor formed at the vaccinated positions and main internal organs. In addition, human liver cancer tumor cells BEL-7402 are used as a positive control group, and $5 \times 10^6$ BEL-7402 cells are injected into each of the 18 mice by the subcutaneous (s.c.) injection. Similarly, the formation of any tumor is observed 30 days after the experiment takes place, and the experiment results are shown in Table 2.

TABLE 2

| Group | No. of Nude mice | No. of Cells | Vaccination Method | Tumor Induction Rate | Tumor Induction Rate of Main Internal Organs |
|---|---|---|---|---|---|
| IKC | 10 | $2 \times 10^7$ | s.c. | 0 | 0 |
| IKC | 10 | $2 \times 10^7$ | i.v. | 0 | 0 |
| BEL-7402 | 18 | $5 \times 10^6$ | s.c. | 100% | 0 |

The experiment results given in Table 2 shows that tumors are formed in all of the 18 nude mice vaccinated with the liver cancer cells BEL-7402 (The tumor induction rate is equal to 100%). Although the nude mice are vaccinated with a vaccination dose of the immune killer cells up to $2 \times 10^7$ cells/mouse, no tumor is formed at the vaccinated positions and main internal organs regardless of the subcutaneous (s.c.) injection or the intravenous (i.v.) injection method, thus showing that the immune killer cells has no tumor induction effect on the nude mice and the method is very safe.

(2) Experiment of Immune Killer Cells on Early Tumor Treatment:

The human liver cancer tumor cells BEL-7402 are removed and vaccinated under the skin at the lateral and back sides of a BALB/c nude mouse (0.1 mL/mouse, containing $5 \times 10^6$ BEL-7402 cells). The treatment by immune killer cells (IKC) starts on the second day after the subcutaneous injection takes place, and the immune killer cells are injected to the tail vein of the nude mouse by the intravenous injection on the $2^{nd}$, $4^{th}$ and $6^{th}$ days (wherein $2 \times 10^7$ cells are injected per mouse). A phosphate buffer solution (PBS) is injected to the control group without performing any other treatment. The mice are sacrificed in 30 days after the vaccination, and the number tumors formed is observed, and the weight of removed tumors is recorded, and the experiment results are listed in Table 3.

TABLE 3

| Group | No. of Nude mice | No. of Cells | Path/Time (days) | Average Tumor Weight (g) | Tumor Suppression Rate % | Tumor Extinction Rate |
|---|---|---|---|---|---|---|
| IKC | 5 | $2 \times 10^7$ | i.v./2, 4, 6 | 0.25 ± 0.31 | 84 ($p < 0.01$) | 3/5 |
| PBS | 5 | | i.v./2, 4, 6 | 1.57 ± 0.46 | | 0 |

The experiment results given in Table 3 shows that tumors are formed in all of 5 mice injected with PBS, and tumors are formed in only 2 out of the 5 mice injected with the immune killer cells (The tumor extinction rate is equal to 60%). In addition, the mice injected with PBS of the control group have an average tumor weight of 1.57 g, and the mice injected with the immune killer cells of the experimental have an average tumor weight of 0.25 g. From the experiment, it shows that the injection of the immune killer cells not only suppresses the formation of early tumors, but also suppresses the growth of tumors, and the tumor suppression rate can be up to 84%, and calculated by the equation given below. Tumor suppression rate (%)=[(Average tumor weight of control group−Average tumor weight of experimental group)/Average tumor weight of control group]×100%

(3) Experiment of Immune Killer Cells on Advanced Tumor Treatment

The experiment method of using the immune killer cells to achieve the effect of suppressing the growth of advanced or larger tumors is described as follows:

In the experiment model of vaccinating the nude mice with human liver cancer tumor cells BEL-7402, the treatment starts when the tumor grows to a diameter approximately equal to 0.5 cm. In the experiment design of the immune killer cells (IKC), there are three groups of PBMC cells and PBS cells, each group includes 5 nude mice. The quantity of immune killer cells and PBMC cells is equal to $2 \times 10^7$ cells/mouse each and the volume is equal to 0.1 mL, and the treatment is made by the intravenous injection method, and only 0.1 mL of PBS is injected for the control group. The injection takes place once every two days for a total of three injections. The tumor growth condition is observed once every two days. The mice are sacrificed in 30 days after the vaccination, and the tumor is removed and weight to calculate a tumor suppression rate, and the experiment results are listed in Table 4.

TABLE 4

| Group | No. of Nude mice | No. of Cells | Path/Time (days) | Average Tumor Weight (g) | Tumor Suppression Rate % | Tumor Extinction Rate |
|---|---|---|---|---|---|---|
| IKC | 5 | $2 \times 10^7$ | i.v./0, 2, 4 | 0.65 ± 0.45 | 70 ($p < 0.01$) | 0/5 |
| PBMC | 5 | $2 \times 10^7$ | i.v./0, 2, 4 | 1.75 ± 0.37 | 18 | 0/5 |
| PBS | 5 | | i.v./0, 2, 4 | 2.14 ± 0.45 | 0 | 0/5 |

Compared with PBS, PBMC without going through the culturing process still has a tumor suppression rate of 18%, but the PBMC gone through the culturing process in accordance with the method of the present invention for 14 days, the cells are called immune killer cells and the tumor suppression rate is increased to 70%, which is 3.9 times of the tumor suppression rate of the PBMC without going through the culturing process.

In summation of the description above, the present invention complies with patent application requirements. The present invention adopts concanavalin A (ConA) as a stimulant for culturing immune killer cells, and no antibody protein is used as the stimulant in the culture process to avoid the risk of being infected by zoonotic diseases and effectively increase the number and specific release of the immune killer cells. The immune killer cells manufactured in accordance with the present invention are used for suppressing the tumor effectively and safely.

It is of course to be understood that the embodiments described herein is merely illustrative of the principles of the invention and that a wide variety of modifications thereto may be effected by persons skilled in the art without departing from the spirit and scope of the invention as set forth in the following claims.

What is claimed is:

1. A manufacturing method of immune killer cells without using antibody protein, comprising steps of:

(a) separating at least one peripheral blood mononuclear cell in a first culture medium, the first culture medium containing concanavalin A (ConA), wherein the concanavalin A (ConA) in the culture medium has a concentration of 0.1-100 μg/mL;

(b) placing the at least one cell in a second culture medium, after the at least one cell is cultured in the first medium for two to six days, wherein the second culture medium contains interleukin and interferon;

(c) adding a third culture medium every 2 to 3 days depending on the cell growing density, wherein the third culture medium contains a lower concentration of interleukin and interferon than the second culture medium; and (d) step (c) is repeated until the total number of culturing days is equal to 14, the immune killer cells containing 5-20% NK cells having the negative phenotype of CD3 and the positive phenotype of CD56, 15-50% NKT cells having the negative phenotype of CD3 and the positive phenotype of CD56, 10-30% γδ T cells wherein the T cells have a γδ T cell receptor, and 40-70% Tc cells wherein the Tc cells are either Tc cells or CTL cells having an αβ T cell receptor.

2. The manufacturing method of immune killer cells according to claim 1, wherein the concanavalin A (ConA) in the first culture medium has a concentration of 0.1-30 μg/mL.

3. The manufacturing method of immune killer cells according to claim 1, wherein multiple peripheral blood mononuclear cells are present in the first culture medium at a concentration of $0.5 \times 10^6$-$2 \times 10^6$ cells/mL.

4. The manufacturing method of immune killer cells according to claim 1, wherein multiple peripheral blood mononuclear cells are present in the second culture medium at a concentration of $0.3 \times 10^6$-$2 \times 10^6$ cells/mL.

5. The manufacturing method of immune killer cells according to claim 1, wherein the first culture medium contains interleukin-2 (IL-2) and interferon-γ.

6. The manufacturing method of immune killer cells according to claim 5, wherein the concentration of interleukin-2 (IL-2) in the first culture medium is 200-100 IU/mL.

7. The manufacturing method of immune killer cells according to claim 5, wherein the concentration of interferon-γ in the first culture medium are 600-1500 units.

8. The manufacturing method of immune killer cells according to claim 1, wherein the second culture medium contains interleukin-2, interferon-γ and interleukin-15.

9. The manufacturing method of immune killer cells according to claim 8, wherein the concentration of interleukin-2 in the second culture medium is 200-600 IU/mL.

10. The manufacturing method of immune killer cells according to claim 8, wherein the concentration of interferon-γ in the second culture medium is 100-300 U/mL.

11. The manufacturing method of immune killer cells according to claim 8, wherein the concentration of interleukin-15 in the second culture medium is 10-50 ng/mL.

\* \* \* \* \*